US006152942A

United States Patent [19]
Brenneman et al.

[11] Patent Number: 6,152,942
[45] Date of Patent: Nov. 28, 2000

[54] VACUUM ASSISTED LANCING DEVICE

[75] Inventors: Allen J. Brenneman, Goshen, Ind.; D. Glenn Purcell, Edwardsburg, Mich.

[73] Assignee: Bayer Corporation, Elkhart, Ind.

[21] Appl. No.: 09/332,082

[22] Filed: Jun. 14, 1999

[51] Int. Cl.[7] .............................. A61B 17/14; A61B 17/32
[52] U.S. Cl. ............................................. 606/181; 606/182
[58] Field of Search .................................. 606/181, 182; 128/765, 770, 329, 637; 604/403

[56] References Cited

U.S. PATENT DOCUMENTS

| | | |
|---|---|---|
| 5,195,534 | 3/1993 | Sarrine ..................................... 128/764 |
| 5,350,392 | 9/1994 | Purcell et al. . | 
| 5,368,047 | 11/1994 | Suzuki et al. . |
| 5,873,887 | 2/1999 | King et al. ................................ 606/182 |

*Primary Examiner*—Michael Buiz
*Assistant Examiner*—Anthony S. King
*Attorney, Agent, or Firm*—Roger N. Coe; Jerome L. Jeffers

[57] ABSTRACT

A vacuum assisted lancing device (10) for obtaining capillary blood from body sites includes a plunger (12) mounted in a barrel or upper housing (24) that upon being pressed by a user, drives a lancet (18) to puncture skin at a body site. A vacuum member such as a diaphragm (38, 66) or bellows (66) is displaced by the plunger (12) and displaces air in the lancing device (10) to create a vacuum. The vacuum draws skin partially into the lancing device (10) causing blood to form at the puncture. The vacuum is then released and the blood is tested.

19 Claims, 6 Drawing Sheets

VACUUM ASSISTED LANCING DEVICE

FIELD OF THE INVENTION

The present invention generally relates to vacuum assisted lancing devices of the type used to draw a sample, i.e. blood or interstitial fluid for testing and, more particularly, to a lancing device having a flexible vacuum member such as a rolling diaphragm or a bellows that displaces air in the lancing device to create a vacuum for drawing capillary blood from a puncture or lancing site.

BACKGROUND OF THE INVENTION

Lancing devices are used for obtaining capillary blood from body sites. A typical user of a lancing device is a person in a program of self-blood glucose monitoring for treatment of diabetes. Such a user presses a lancing device at a selected puncture site, activates the lancing device to puncture the skin at the site, and draws capillary blood for testing. To minimize any discomfort caused by the puncture, the lancing device typically controls the depth of the puncture, quickly withdraws the lancet from the skin once a puncture has been made, and prevents the lancet from rebounding and reentering the puncture or causing a second puncture.

Once a puncture has been made, the lancing device remains on the site and a vacuum is created to draw skin partially into an end cap of the device. As this occurs, a small amount of blood forms on the skin at the puncture. The vacuum is then released and the lancing device is removed from the skin. The drop of blood on the surface of the skin at the puncture site is then applied to a test sensor.

These lancing devices include a gasket connected to the lancet that reciprocates in the lancing device as the lancet moves through a lancing stroke. The gasket is in airtight contact with the inside of the lancing device such that as the gasket slides within the lancing device, air is displaced and a vacuum is created. The necessity for the airtight contact between the gasket and the inside of the lancing device requires precision molding of the parts which increases the cost of the device.

In addition, friction between the gasket and lancet device reduces the speed of the lancet which can increase the pain experienced by a user. This friction also increases the force required to actuate the lancet making the lancet device harder to operate. Also, the airtight fit can quickly start to leak if dirt gets between the gasket and the lancet device. A gasket also limits the configuration of the devices to a round shape and may limit the possible uses of the lancet devices as part of a test sensor.

SUMMARY OF THE INVENTION

The present invention is directed to a vacuum assisted lancing device used to obtain capillary blood or other body fluids from body sites. The lancing device includes a housing with an open end. The open end is intended to be firmly pressed against the skin at a selected lancing site. A lancet holder is mounted in the housing for reciprocating movement toward and away from the open end of the housing. A lancet which punctures the skin at the lancing site is mounted in the holder.

The lancing device also includes a plunger that a user presses to actuate the device. Springs in the lancing device are extended and compressed by the movement of the plunger to drive the lancet into the skin of a user at a lancing site and withdraw the lancet without rebound. After the skin has been punctured, a vacuum is created in the lancing device which causes the skin in the open end of the device to bulge slightly into the device. This vacuum is created by the displacement of a vacuum member in the lancing device. The vacuum member can be a rolling diaphragm, a bellows or similar member that can be displaced by movement of the plunger. As the vacuum member is displaced, air in the lancing device is displaced creating a vacuum. The vacuum causes blood or other body fluids to form at the puncture. The vacuum is then released the lancing device removed from the site, and the fluid touched to a test sensor for testing.

BRIEF DESCRIPTION OF THE DRAWINGS

Other objects and advantages of the invention will become apparent upon reading the following detailed description and upon reference to the drawings in which.

DETAILED DESCRIPTION OF ILLUSTRATIVE EMBODIMENTS

Figure 1:
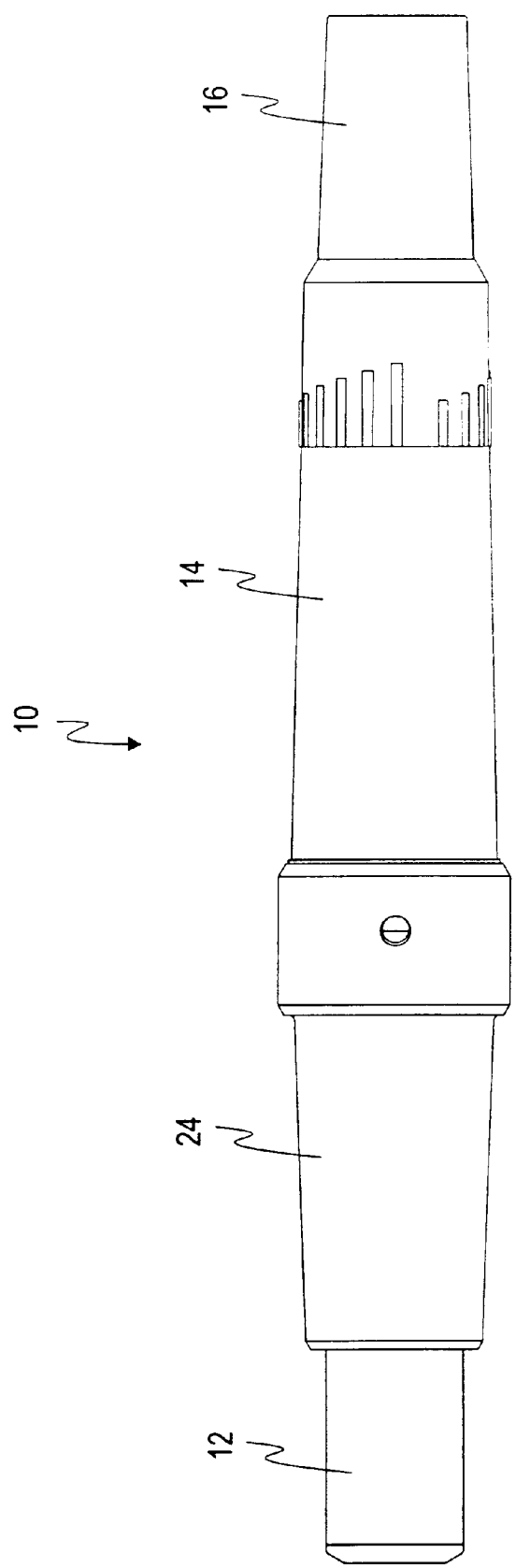
FIG. 1 is a view of a vacuum assisted lancing device constructed in accordance with the principles of the present invention.

Vacuum assisted lancing devices are used for obtaining capillary blood or other body fluids from body sites and preferably body sites other than fingertips. These devices drive a lancet into the skin at a chosen body site. A vacuum is then created in the device at the body site causing blood or fluid to form at the skin surface The blood is touched to a test sensor for a desired test such as for the determination of blood glucose.

The vacuum mechanism in known lancing devices has an air tight fit with the inside surface of the lancing device which requires precision molding of the parts to ensure sufficient vacuum is created. The vacuum mechanism adds several parts to the lancing device. The vacuum mechanism typically is coupled to a plunger that is depressed by an operator. Friction resulting from the air tight fit increases the force required to operate the plunger. Also, as a result of wear and debris, these vacuum devices have difficulties holding and controlling the vacuum.

The vacuum assisted lancing device of the present invention is generally designated by the reference number 10 in the drawings. The vacuum assisted lancing device 10 is shown as a handheld model; however, a flexible vacuum member provided in the vacuum assisted lancing device 10 allows the lancing device 10 to take on many different shapes such as rectangular, square and oval. This allows the vacuum assisted lancing device 10 to be an integral component of a test sensor.

Figure 2:
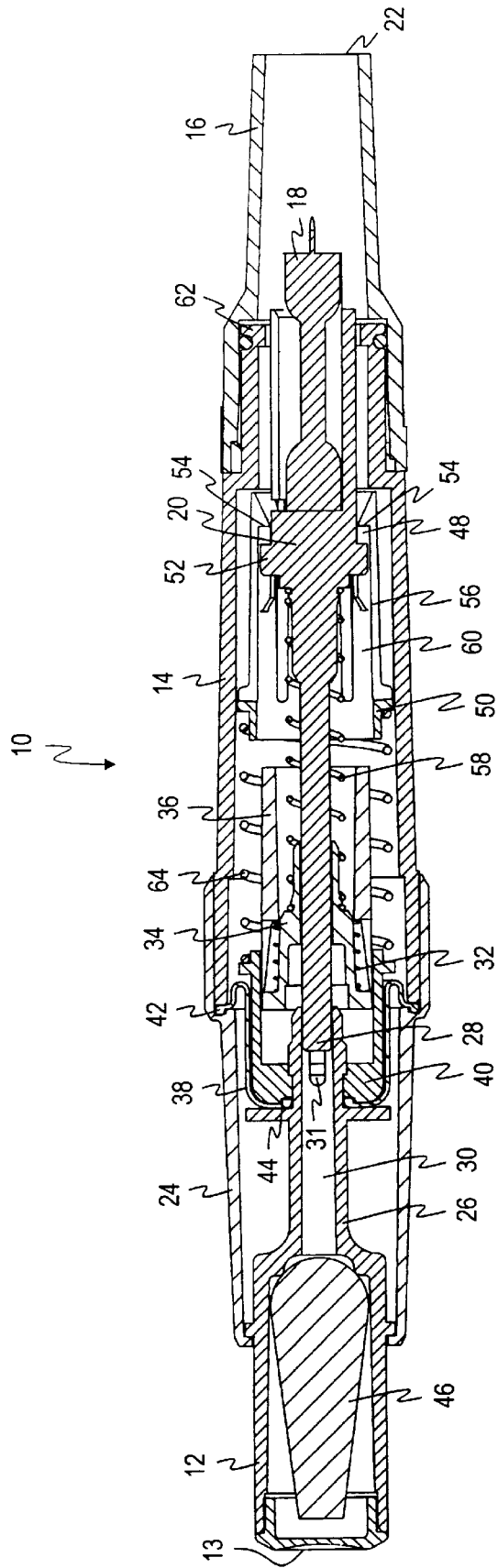
FIG. 2 is an enlarged, cross-sectional view of the lancing device in a static position.

The vacuum assisted lancing device 10 includes the usual outer components such as a plunger 12, an upper housing 24, a barrel or lower housing 14, and an end cap 16. A person using the vacuum assisted lancing device 10 selects and prepares a puncture or lancing site, removes the end cap 16, inserts a lancet 18 in a lancet holder 20, (FIG. 2). replaces the end cap 16, and firmly presses the end cap 16 against the skin at the selected puncture or lancing, site to form an airtight seal as with the skin. The site is lanced by pressing the plunger 12 until it comes to a complete stop. The plunger 12 is then slowly released and a vacuum is created in the end cap 16 causing the skin in the end cap to bulge slightly into the end cap 16. Blood or other fluid forms on the surface of the skin at the puncture. The plunger 12 is then pressed down to release the vacuum and the vacuum assisted device 10 is removed from the puncture or lancing site. The fluid can be touched or put into contact with a test sensor where the desired tests are performed.

Turning now to the internal components of the lancing device 10, these can best be described in conjunction with a description of the operation of the lancing device 10. The lancing device 10 is shown in its static or at rest position in FIG. 2. In the static position, the lancet 18 is inside the end cap 16 spaced a distance away from an open end 22 of the end cap 16. To use the lancing device 10. the open end 22 of the end cap 16 is pressed against the skin at a lancing site of a person whose blood is to be tested. To actuate the lancing device, end portion 13 is pressed causing plunger 12 to be pushed into the upper housing 24 of the lancing device 10. The plunger 12 is hollow and includes a hollow stem 26. An upper end 28 of the lancet holder 20 extends into the hollow interior 30 of the stem 26.

During the first portion of travel of the plunger 12, a rebound spring 32 captured between a return 34 and a release 36 is expanded or extended and a rolling diaphragm 38 is displaced toward the end cap 16. The rebound spring 32 functions to pull the lancet 18 away from the lancing site after a puncture to avoid painful rebound punctures. A piston 40 is secured to the release 36 and the hollow stem 26 of the plunger 12. Through this connection, the release 36 is moved away from the return 34 during the first portion of plunger travel extending the rebound spring 32.

Figure 4:
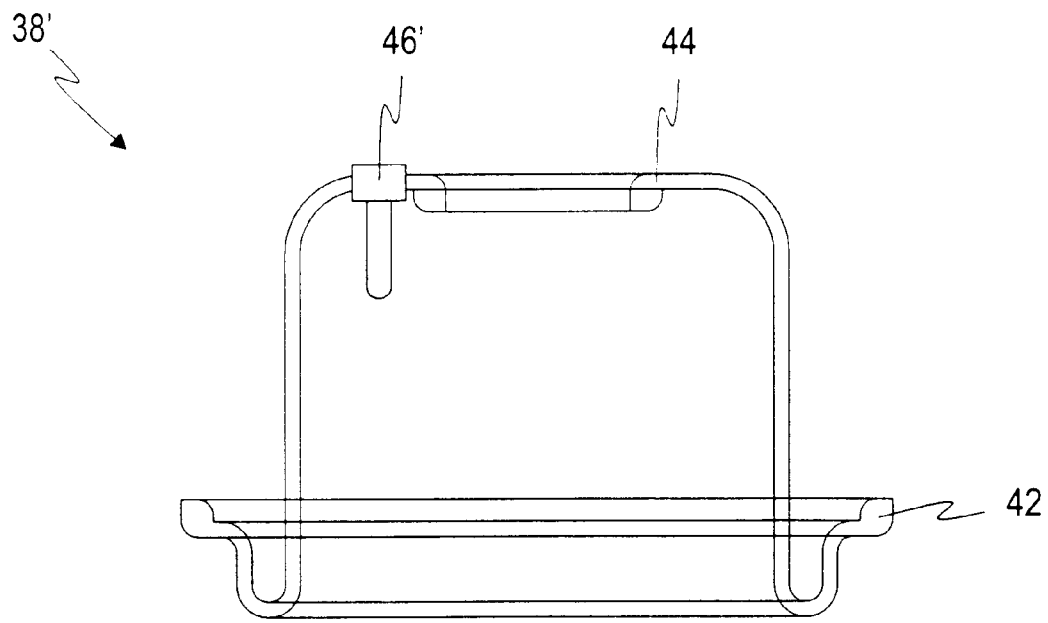
FIG. 4 is an enlarged side view of a rolling diaphragm with a one way valve.
Figure 5:
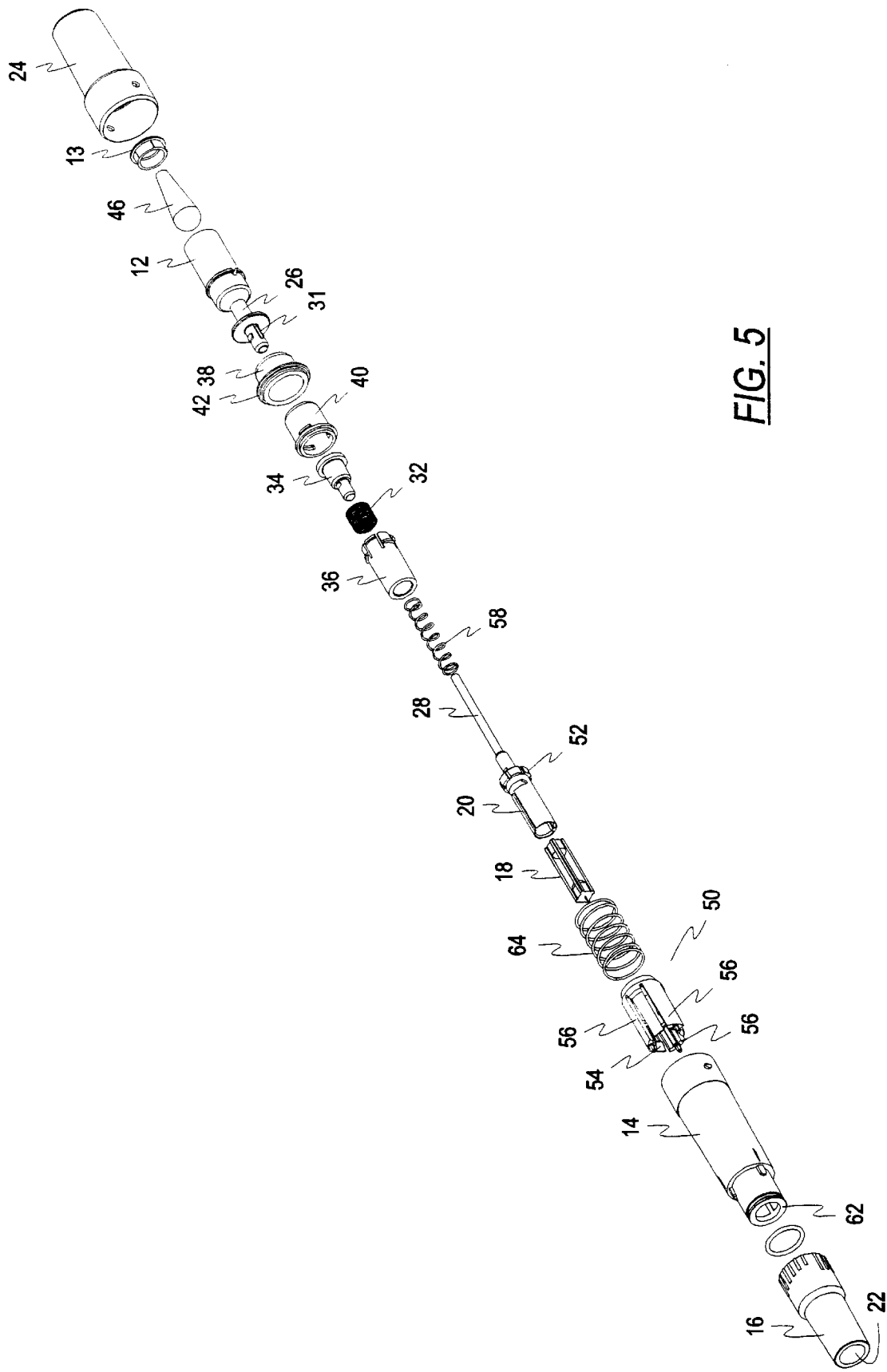
FIG. 5 is an exploded perspective view of the lancing device.

An annular rim 42 of the rolling diaphragm 38 is captured between the upper housing 24 and the lower housing 14 of the lancing device 10 thus anchoring the annular rim 42 relative to the lancing device 10. A central portion 44 of the diaphragm 38 is secured to the hollow stem 26 and piston 40 such that the central portion 44 moves with the plunger 12 relative to the upper housing 24 and lower housing 14. The securements of the diaphragm 38 to the stem 26 and the upper and lower housings 24 and 14, respectively are air tight. Thus, as the plunger 12 is pushed into the upper housing 24, compressed air may pass through openings 31 in a stem 26 through the hollow interior 30 and a one way seal or valve 46. Alternatively. a diaphragm 38' (FIG. 4) may be used that includes a one way valve 46' in the body of the diaphragm 38'.

Also, during the first portion of plunger travel a gap 48 (FIG. 2) between the lancet holder 20 and a latch 50 is closed as a flange 52 on the lancet holder 20 moves toward and engages inner edges 54 of a plurality of latch fingers 56 formed on the latch 50. After the gap 48 closes, a drive spring 58 is compressed between the lancet holder 20 and the return 34.

Once the flange 52 engages the inner edges 54, the travel of the lancet holder 20 is halted. Continued travel of the plunger 12 moves the release 36 into the latch 50 up to and along ramps 60 formed on the inner periphery of the latch 50 at each finger 56. The movement of the release 36 along the ramps 60 spreads the fingers 56 releasing the lancet holder 20. Once the lancet holder 20 is released the drive spring 58 drives the lancet holder 20 and the lancet 18 out the open end 22 of the end cap 16. Travel of the lancet holder 20 and lancet 18 is limited by a stop or rim 62 formed on the lower housing 14 at a location to engage the flange 52 on the lancet holder 20. The location of the stop 62 controls the depth of penetration of the lancet 18 into the skin at the lancing site.

Figure 3:
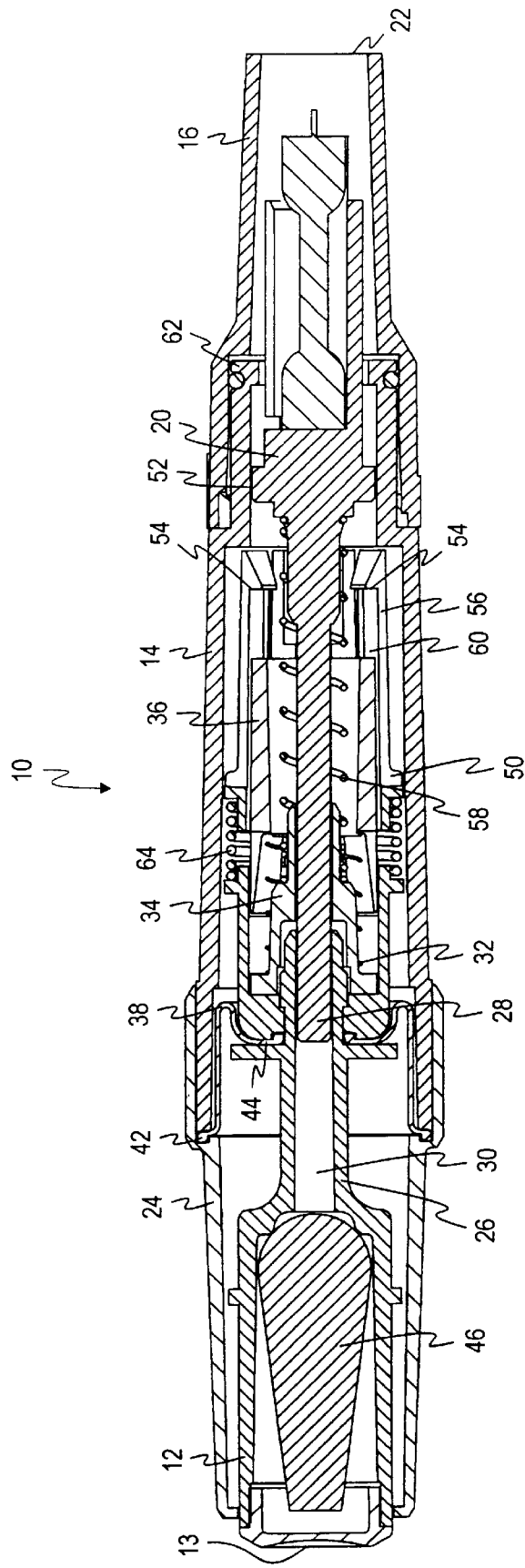
FIG. 3 is an enlarged, cross-sectional view of the lancing device in a position after a lancet has been driven and before a vacuum is created.

As the lancet 18 extends out of the open end 22 of the end cap 16, the drive spring 58 is extended. Upon engagement of the flange 52 with the stop 62, the drive spring 58 begins to return to its static or unextended position pulling the lancet 18 and lancet holder 20 into the end cap 16 and lower housing 14. The rebound spring 32 also returns to its original position pulling the lancet 18 and lancet holder 20 into the lancing device 10 and preventing a rebound puncture. The rebound spring 32 is compressed to its static position by the drive spring 58. The configuration of the lancing device 10 at this point in the operation is shown in FIG. 3.

Pressure on the plunger 12 can be slowly released while the open end 22 of the end cap 16 is held against the skin at the lancing site. The plunger 12 is moved out of the upper housing 24 by a return spring 64 located between the piston 40 and the latch 50. The return spring 64 is compressed during the inward travel of the plunger 12. As the plunger 12 is moved out of the upper housing 24. the diaphragm 38 is pulled toward its static position. The openings 31 are closed by the upper end 28 of the lancet holder 20 and the displacement of the diaphragm 38 displaces air in the lower housing 14 creating a vacuum. This vacuum causes skin at the lancing site to bulge slightly into the end cap 16. A drop of body fluid will then form at the puncture. The plunger 12 may then be pressed into the upper housing 24 displacing the diaphragm 38 away from its static position and reducing the vacuum in the lower housing 14. The lancing device 10 may then be removed from the lancing site and the body fluid may be introduced into a test sensor.

The rolling diaphragm 38 replaces a precision bore, piston and O-ring used in prior art lancing devices to create a vacuum. The diaphragm 38 eliminates the need for precision molding of the bore and piston required in prior art lancing devices, reduces the number of parts that must be assembled, and eliminates the friction caused by the interference fit of the O-ring and the bore reducing the force needed to operate the device. The diaphragm 38 is not susceptible to dirt which can get between piston/bore and O-ring components of the prior art devices and cause vacuum leaks.

Figure 6:
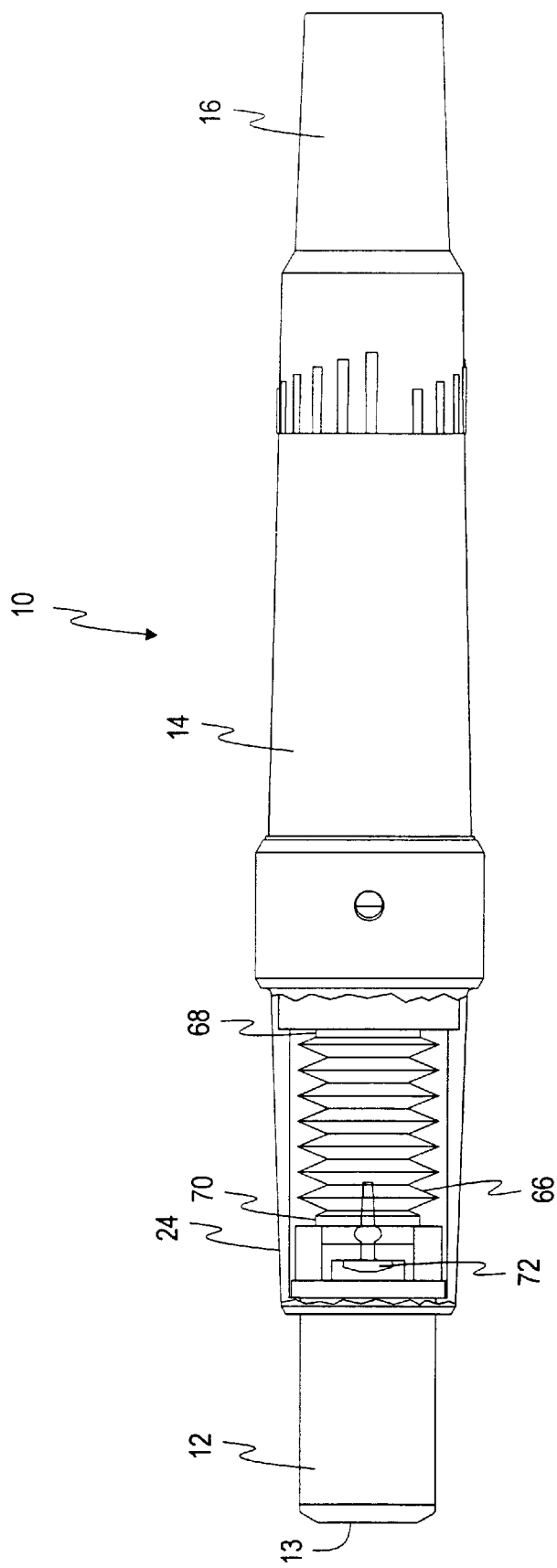
FIG. 6 is a view of an alternative embodiment of the lancing device with a bellows in place of a rolling diaphragm.

Other vacuum devices can be used instead of the diaphragm 38. For example, a bellows 66 can be used (FIG. 6). A first end 68 of the bellows 66 is secured to the upper housing 24 and a second end 70 of the bellows 66 is secured to the plunger 12. As the plunger 12 is moved into the upper housing 24, the second end 70 is displaced toward the first end 68 and displaced air is vented through one way check valve 72 in the bellows 66. As the plunger 12 moves back toward its static position, a vacuum is created similar to that created by the diaphragm 38.

The diaphragm 38 or bellows 66 can be any of several shapes such as round, oval, square or rectangular. This provides design flexibility allowing the lancing device 10 to be integrated into a meter such as a glucose meter without greatly increasing the overall size of the meter.

While the present invention has been described with reference to the particular embodiments illustrated, those skilled in the art will recognize that many changes and variations may be made thereto without departing from the spirit and scope of the present invention. The embodiments and obvious variations thereof are contemplated as falling within the scope and spirit of the claimed invention, which is set forth in the following claims:

What is claimed is:

1. A vacuum assisted lancing device (10) comprising:
   a housing (14, 24) having an open end (22);
   a lancet holder (20) mounted in said housing;
   a first resilient member (58) mounted in said housing (14, 24) and associated with said lancet holder (20) to bias said lancet holder (20) toward said open end (22) of said housing (14, 24);
   a second resilient member (32) mounted in said housing associated with said lance holder (20) to bias said lancet holder (20) away from said open end (22) of said housing (14; 24) and
   a flexible vacuum member (38, 66) in said housing associated with said lancet holder (20) and flexed, after said lancet holder (20) is biased away from said open end (22), to displace air in said housing (14, 24).

2. The vacuum assisted lancing device (10) claimed in claim 1 wherein at least a portion (42) of said flexible vacuum member (38, 66) is secured to said housing (14, 24).

3. The vacuum assisted lancing device (10) claimed in claim 1 wherein a first portion (42) of said flexible vacuum member (38, 66) is secured to said housing (14, 24) and a second portion (44) of said flexible vacuum member (38, 66) is flexible relative to said housing (14, 24).

4. The vacuum assisted lancing device (10) claimed in claim 1 wherein said flexible vacuum member is a diaphragm (38).

5. The vacuum assisted lancing device (10) claimed in claim 1 wherein said flexible vacuum member is a bellows (66).

6. The vacuum assisted lancing device (10) claimed in claim 1 further comprising a one way check valve in said flexible vacuum member (38, 66).

7. A vacuum assisted lancing device (10), comprising:
   a housing (14, 24) with an open end (22);
   a lancet holder (20) moveably mounted in said housing (14, 24) adjacent said open end (22);
   an actuator (12) coupled to said lancet holder (20) for moving said lancet holder (20) toward said open end (22);
   at least one resilient member (32) coupled to said lancet holder (20) biasing said lancet holder (20) away from said open end (22); and
   a vacuum member in said housing (38, 66) associated with and flexed, after said lancet holder (20) is biased away from said open end (22), by at least one of said actuator (12) and said lancet holder (20).

8. The vacuum assisted lancing device (10) claimed in claim 7 wherein at least a portion (42) of said vacuum member (38, 66) is secured to said housing (14, 24).

9. The vacuum assisted lancing device (10) claimed in claim 7 further comprising a one way check valve (46) in said housing (14, 24).

10. The vacuum assisted lancing device (10) claimed in claim 7 further comprising a one way check valve (46) in said vacuum member (38, 66).

11. The vacuum assisted lancing device (10) claimed in claim 7 wherein said vacuum member is a rolling diaphragm (38).

12. The vacuum assisted lancing device (10) claimed in claim 7 wherein said vacuum member is a flexible bellows (66).

13. The vacuum assisted lancing device (10) claimed in claim 7 wherein said resilient member is a spring (32).

14. A method of drawing a body fluid sample for testing using a vacuum assisting a lancing device (10), comprising:
   providing a housing (14, 24) having at least one open end (22);
   mounting a lancet holder (20) and a lancet (18) in said housing (14, 24) adjacent said open end (22) for reciprocating movement in said housing;
   securing at least a first portion (42) of a flexible member (38, 66) to said housing (14, 24);
   securing a second portion (44) of said flexible member (38, 66) to move with said lancet holder (20);
   placing the open end (22) against a Selected puncture site;
   moving said lancet holder (20) and said lancet (18) through said open end (22) and propelling said lancet (I8) into said puncture site and retracting said lancet (18) from said puncture site; and
   flexing said flexible member (38, 66) to displace air in said housing and draw a body fluid sample from said puncture site.

15. The method of drawing a body fluid sample using a vacuum assisting a lancing device (10) as set forth in claim 14 wherein said flexible member is a rolling diaphragm (38) and said flexing comprises rolling said diaphragm (38) in said housing (14, 24).

16. The method of drawing a body fluid sample using a vacuum assisting a lancing device (10) as set forth in claim 14 wherein said flexible member is a bellows (66) and said flexing comprises flexing of said bellows (66).

17. The method of drawing a body fluid sample using a vacuum assisting a lancing device (10) as set forth in claim 14 further comprising displacing at least some air in said housing (14, 24) one way through said flexible member (38, 66).

18. The method of drawing a body fluid sample using a vacuum assisting a lancing device (10) as set forth in claim 14 comprising pressing said at least one open end (22) of said housing (14, 24) against a portion of a user's body prior to moving said lancet holder (20) toward said open end (22).

19. The method of drawing a body fluid sample using a vacuum assisting a lancing device (10) as set forth in claim 14 wherein said flexible member (38, 66) having a first end (44) and second end (42), said flexing comprising displacing said first end (44) of said flexible member (38 66) relative to said second end (42) of said flexible member (38, 66).

* * * * *